United States Patent
Wisniewski et al.

(10) Patent No.: US 7,816,489 B2
(45) Date of Patent: Oct. 19, 2010

(54) METHODS FOR MAKING INTERMEDIATES AND OXYTOCIN ANALOGUES

(75) Inventors: Kazimierz Wisniewski, San Diego, CA (US); Jacek Stalewski, San Diego, CA (US); Guangcheng Jiang, San Diego, CA (US)

(73) Assignee: Ferring B.V., Hoofddorp (NL)

( * ) Notice: Subject to any disclaimer, the term of this patent is extended or adjusted under 35 U.S.C. 154(b) by 223 days.

(21) Appl. No.: 11/929,494

(22) Filed: Oct. 30, 2007

(65) Prior Publication Data

US 2008/0177035 A1 Jul. 24, 2008

Related U.S. Application Data

(60) Division of application No. 11/457,743, filed on Jul. 14, 2006, now Pat. No. 7,304,181, which is a division of application No. 10/888,704, filed on Jul. 8, 2004, now Pat. No. 7,091,314, which is a continuation of application No. PCT/US03/004301, filed on Feb. 13, 2003.

(60) Provisional application No. 60/360,345, filed on Feb. 27, 2002.

(51) Int. Cl.
*C07K 7/06* (2006.01)
*C07K 7/00* (2006.01)
*C07K 1/04* (2006.01)

(52) U.S. Cl. ................... 530/329; 530/315; 530/317; 530/330; 530/333

(58) Field of Classification Search ................ None
See application file for complete search history.

(56) References Cited

U.S. PATENT DOCUMENTS

| 5,656,721 | A | 8/1997 | Albert et al. |
| 6,114,310 | A | 9/2000 | Chamberland et al. |
| 6,143,722 | A | 11/2000 | Melin et al. |
| 6,245,746 | B1 | 6/2001 | Chamberland et al. |
| 6,346,601 | B1 | 2/2002 | Obiols et al. |
| 6,436,980 | B1 | 8/2002 | Leger et al. |

FOREIGN PATENT DOCUMENTS

| WO | WO 92/00996 | 1/1992 |
| WO | WO 95/02609 | 1/1995 |
| WO | WO 03/000692 | 1/2003 |

OTHER PUBLICATIONS

Kawai et al, "Poly-L-Homocysteine", Polymer Journal (1976), vol. 8, No. 2, pp. 158-166.
Prochazka et al., "Analongs of Deamino Carba Oxytocin With Inhibitory Properties; Synthesis and Biological Activities", Collection of Czechoslovak Chemical Communications (1992), vol. 57, pp. 1335-1344.

*Primary Examiner*—Julie Ha
(74) *Attorney, Agent, or Firm*—Fitch, Even, Tabin & Flannery

(57) ABSTRACT

More efficient and/or economical methods for synthesizing heptapeptide alcohol analogs of oxytocin are provided along with novel intermediates which are useful in synthesizing such oxytocin analogs. Efficient and economical methods for synthesizing intermediates useful in synthesizing these oxytocin analogs are also provided.

9 Claims, No Drawings

METHODS FOR MAKING INTERMEDIATES AND OXYTOCIN ANALOGUES

This application is a divisional of U.S. Ser. No. 11/457,743 filed Jul. 14, 2006, which is a divisional of U.S. Ser. No. 10/888,704, filed Jul. 8, 2004, now U.S. Pat. No. 7,091,314 which is a continuation of PCT/US03/04301, filed Feb. 13, 2003, which claims priority from U.S. Provisional Application Ser. No. 60/360,345, filed Feb. 27, 2002, the disclosures of all of which are incorporated herein by reference.

FIELD OF THE INVENTION

The present invention relates to methods for making intermediates and using same to make equivalent heptapeptide alcohol analogues of desamino-oxytocin (i.e. cyclic peptides wherein the N-terminal residue is deaminated and the C-terminus is an alcohol). Improved methods are disclosed for synthesizing intermediates and for employing these intermediates to produce the analogues that exhibit oxytocin antagonist activity and that are useful, inter alia, for decreasing or blocking uterus muscle contraction.

BACKGROUND OF THE INVENTION

Oxytocin is a peptide hormone which stimulates contraction of the uterine muscles, and it is believed to be involved in the etiology of pre-term labor and dysmenorrhea. Oxytocin antagonists have proved to be useful in the control of these conditions, and oxytocin antagonist peptides of good potency and selectivity for therapeutic use are disclosed in WO 95/02609, published 26 Jan. 1995. They are often intended for administration in aqueous solution, and the manufacture of ready-for-use doses of such antagonists may require that such solutions be stable for extended periods; which they may not always be. The potential need to prepare such a medicament immediately prior to use was considered to be inconvenient and generated an improvement.

U.S. Pat. No. 6,143,722 (EP 938,496; WO 98/23636) discloses equivalent heptapeptide analogues that exhibit oxytocin antagonist activity, which resemble those disclosed in the earlier WO 95 application, but wherein the C-terminus of the peptide is reduced to an alcohol. By heptapeptide or equivalent heptapeptide, for purposes of this application, is meant a cyclic compound where the N-terminal residue is deaminated and its side chain is linked by a covalent bond to a side chain of a residue spaced apart therefrom in the peptide chain which contains 6 residues in addition to the N-terminal residue.

Although such oxytocin antagonist peptides can be synthesized by the synthesis disclosed in the '722 patent, it requires about 7 separate steps, counting the peptide synthesis as one and not counting the synthesis of the modified homocysteine (Hcy) residue. More economical syntheses are frequently sought for chemical compounds of potential commercial interest, and such is the case in this instance.

SUMMARY OF THE INVENTION

The present invention provides new intermediate compounds and new methods for making certain intermediate compounds that are useful in synthesizing pharmaceuticals, particularly oxytocin antagonist peptides of the general type taught in the '722 U.S. patent. The invention also provides improved methods for synthesizing the oxytocin antagonist peptide alcohols disclosed in the '722 patent, which syntheses permit more efficient and economical production of such C-terminal alcohol peptides.

In a more specific aspect, the invention provides an intermediate suitable for forming a peptide having pharmaceutical properties, which has the formula:

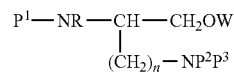

wherein $P^1$ is H or an amino-protecting group; $P^2$ is an amino-protecting group that is different than $P^1$ and is not labile under conditions that would remove $P^1$; $P^3$ is H or an amino-protecting group that is different than $P^1$ and is not labile under conditions that would remove $P^1$, provided however that $P^2$ and $P^3$ may be a divalent amino-protecting group; n is 2, 3 or 4; R is lower alkyl; and W is H, a protecting group or resin; and also provides a method for making such an intermediate wherein an α-amino acid having an amino side chain, with its side chain amino group protected and its α-amino group acylated, is reacted in a suitable solvent with a reducing agent to change the acyl group to an alkyl group and simultaneously change the α-carboxy group to $CH_2OH$.

In another specific aspect, the invention provides a method for preparing an equivalent heptapeptide analogue, or a pharmaceutically acceptable salt thereof, having oxytocin antagonist activity and consisting of a hexapeptide moiety A and a C-terminal β-aminoalcohol residue B bound to the moiety A by an amide bond, wherein (1) the β-aminoalcohol B is:

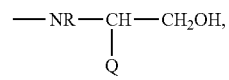

with Q being $(CH_2)_n$—$NH_2$, with n being 2, 3 or 4, and R being $CH_3$ or $C_2H_5$; and (2) the moiety A is:

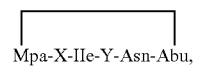

with X being a D-aromatic α-amino acid, which may optionally have its side chain protected; and Y being an aliphatic α-amino acid, which method includes the following steps:
(a) providing a resin-linked diamino alcohol having the formula:

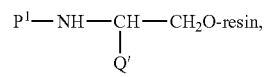

wherein $P^1$ is H or an amino-protecting group, Q' is $(CH_2)_n$—$NP^2P^3$, with n being 2, 3 or 4, $P^2$ being an amino-protecting group that is different from $P^1$ and not labile under conditions that would remove $P^1$, and $P^3$ being H or an amino-protecting group that is the same or different than $P^2$, provided however that $P^2$ and $P^3$ may be a divalent amino-protecting group, and with the resin being one capable of forming an ether bond with an aliphatic alcohol; (b) N-alkylating to produce the compound:

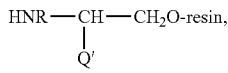

wherein R is $CH_3$ or $C_2H_5$; (c) adding residues either singularly or in a group or groups to create the following peptide-resin:

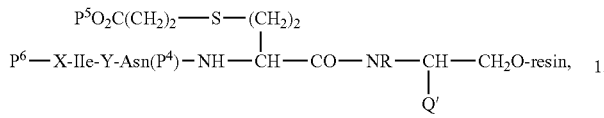

wherein $P^4$, $P^5$ and $P^6$ are individually H or protecting groups; (d) cleaving from the resin and selectively deprotecting to remove any protecting groups $P^4$, $P^5$ and $P^6$ to form the linear compound:

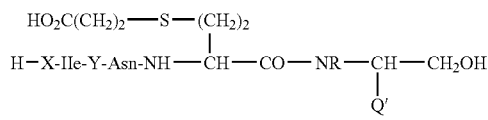

(e) cyclizing the linear compound to create the compound:

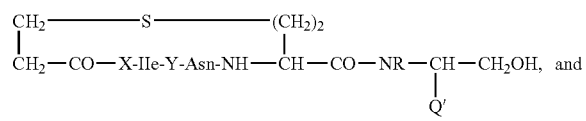

(f) deprotecting to create the cyclic equivalent hexapeptide:

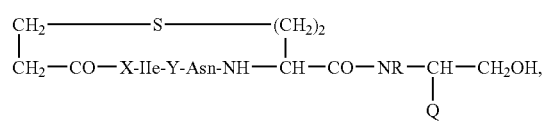

wherein Q is $(CH_2)_n$—$NH_2$

In a further more specific aspect, the invention provides a method for preparing an equivalent heptapeptide analogue, or a pharmaceutically acceptable salt thereof, having oxytocin antagonist activity and consisting of a hexapeptide moiety A and a C-terminal β-aminoalcohol residue B bound to the moiety A by an amide bond, wherein (1) the β-aminoalcohol B is:

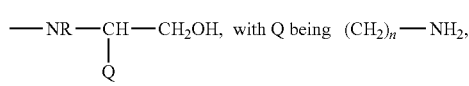

with n being 2, 3 or 4, and R being $CH_3$ or $C_2H_5$; and (2) the moiety A is:

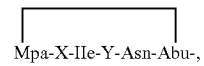

and with X being a D-aromatic α-amino acid, which may optionally have its side chain protected; and Y being an aliphatic α-amino acid, which method includes the following steps: (a) providing a resin-linked amino acid having the formula:

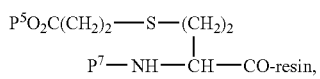

wherein $P^5$ is a protecting group and $P^7$ is H or a protecting group;

(b) adding residues either singularly or in a group or groups to create the following peptide-resin:

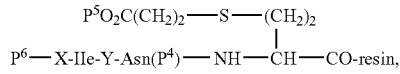

wherein $P^4$ and $P^6$ are individually protecting groups;
(c) cleaving from the resin to form the linear compound:

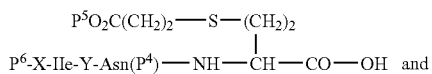

(d) coupling

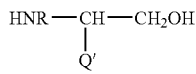

to form the linear compound:

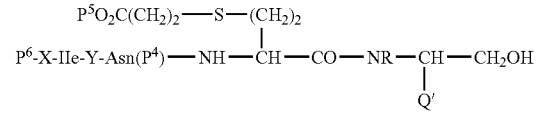

wherein Q' is $(CH_2)_n$—$NP^2P^3$, with n being 2, 3 or 4, $P^2$ being an amino-protecting group, and $P^3$ being H or an amino-protecting group that is the same or different than $P^2$, provided however that $P^2$ and $P^3$ may be a divalent amino-protecting group;

(e) selectively deprotecting and cyclizing the linear compound to create the compound:

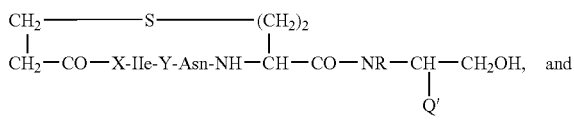

(f) deprotecting to create the cyclic equivalent heptapeptide:

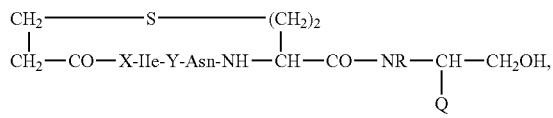

wherein Q is $(CH_2)_n—NH_2$.

DETAILED DESCRIPTION OF THE PREFERRED EMBODIMENTS

The present invention provides improved methods for synthesizing such equivalent heptapeptide analogues exhibiting therapeutically useful oxytocin antagonist activity and improved stability in aqueous media. These equivalent heptapeptide analogues are characterized by a structure which comprises an N-terminal hexapeptide analogue moiety A and a C-terminal diaminoalcohol moiety B. The structure of the diaminoalcohol moiety B is:

(B)

wherein Q is $—(CH_2)_nNH_2$, with n being 2, 3 or 4, and R is $CH_3$ or $CH_2H_5$.

The structure of the moiety A is:

(A)

wherein Mpa, Ile, Asn and Abu have the following meanings:

Mpa 3-mercaptopropionic acid residue (otherwise called desamino-cysteine)
Ile isoleucine residue
Asn asparagine residue
Abu α-aminobutyric acid residue;
and wherein
X is a D-aromatic α-amino acid residue; and
Y is an aliphatic α-amino acid residue.

By an aromatic α-amino acid is meant an α-amino acid wherein the side chain includes an aromatic ring system. Such a system may be carbocyclic or heterocyclic, monocyclic or fused. Examples of aromatic α-amino acids include (but are not limited to) phenylalanine, tyrosine, (O-ethyl)tyrosine, tryptophan, β-(2-naphthyl)alanine and phenylglycine, and the residue X is of the unnatural D-configuration.

By an aliphatic α-amino acid is meant an α-amino acid of the natural L-configuration wherein the side chain has only carbon and hydrogen atoms. Such side chains may include alkyl and cycloalkyl groups; they may be unsaturated but may not include aromatic residues. The side chains may have 1 to 12 carbon atoms, although the preferred range is 3-7 carbon atoms. Examples of aliphatic α-amino acids include alanine, valine, leucine, isoleucine, alloisoleucine (alle), cyclohexylglycine, (β,β-diethyl) alanine and adamantylalanine.

In the structure of the hexapeptide analogue moiety A, the line joining the Mpa and Abu residues has its conventional meaning, signifying that there is a covalent bond linking the ends of the side chains of these two residues. In this case, a sulfur atom at the end of the side chain of the N-terminal Mpa residue is joined by a covalent bond to the γ-(or 4-) carbon atom of the Abu residue side chain.

The diaminoalcohol moiety B includes a stereogenic centre, so it can exist in two epimeric forms, R and S, corresponding to the D and L isomers of the related amino acids. Heptapeptide analogues with either of these isomers are acceptable, as are mixtures of epimers. Preferably, the diaminoalcohol moiety is present as a single epimer, and more preferably it has the S configuration.

In the context of the present application, the Mpa residue and the diaminoalcohol B are considered to be equivalents of α-amino acids; thus, the compounds of interest are termed heptapeptides or equivalent heptapeptides.

In preferred compounds, X is either a D-tryptophan residue or a β(2-naphthyl)-D-alanine residue, Y is a residue of valine, leucine, isoleucine, alloisoleucine, cyclohexylalanine, or (β,β-diethyl)alanine.

Some of the particularly preferred compounds are the following:

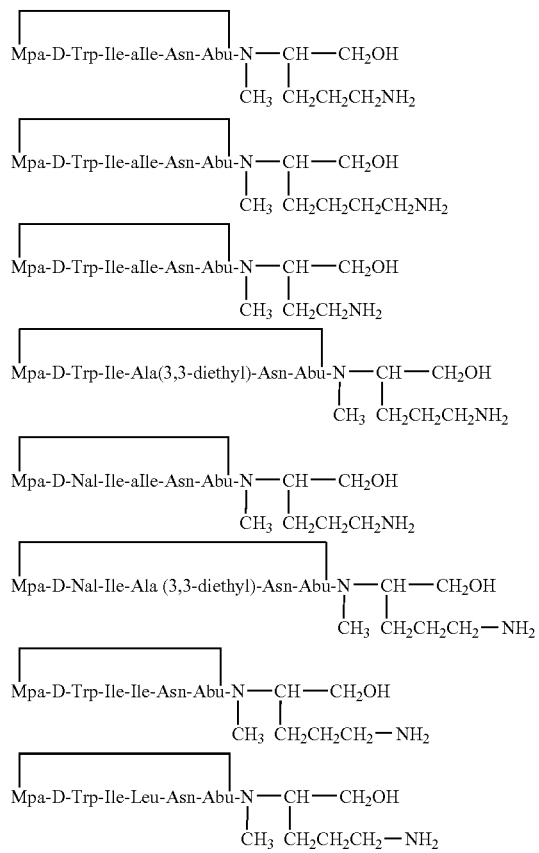

-continued

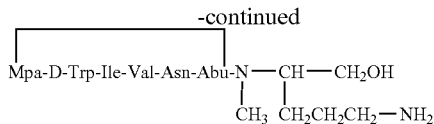

wherein the following further abbreviations have been used:
D-Trp D-tryptophan residue
aIle alloisoleucine residue
Ala(3,3-diethyl) (β,β-diethyl)alanine residue
D-Nal β-(2-naphthyl)-D-alanine residue
Leu leucine residue
Val valine residue The first peptide listed above is presently the most preferred compound.

These peptides of interest contain a basic site (amine) and so can form salts with acids, which salts retain the pharmacological properties of the free bases. Examples of such salts include (but are not limited to) the hydrochloride, hydrobromide, sulfate, acetate, citrate, benzoate, trifluoroacetate and methanesulfonate. The methods disclosed are useful steps in producing pharmaceutical compositions which include a pharmacologically effective amount of at least one of the oxytocin antagonist heptapeptide analogues described above. Such compositions may include pharmaceutically acceptable additives or carriers, such as preservatives, diluents, dispersing agents, agents to promote mucosal absorption, buffering agents and flavorings, such as disclosed in the '722 patent and may be so administered for reducing or blocking the contraction of the uterine muscle. One preferred composition is a sterile aqueous solution of such a heptapeptide analogue in isotonic saline, which is suited to intranasal administration or intravenous injection, containing a buffering agent, e.g. a phosphate/citrate buffer, to maintain the pH of the solution in the range 0.3-7.0, and preferably in the range 3.5-5.5. With respect to routes of administration, intravenous or subcutaneous injections are likely to be the most efficient routes of delivery, while intranasal administration can be expected to be more efficient than oral dosing. Generally, the amount of compound constituting a single effective dose for intravenous or subcutaneous treatment of an average woman in pre-term labor is from about 0.1 mg to about 500 mg, and preferably from about 1 mg to about 200 mg, in a period of 24 hours. The invention provides improved methods of synthesizing such oxytocin antagonist heptapeptide analogues and intermediates for use in such syntheses, which methods are more economical than prior art methods and/or have higher yields.

These overall methods for preparing a heptapeptide analogue of interest, or a pharmaceutically acceptable salt thereof, having oxytocin antagonist activity generally comprise making a compound that consists of a hexapeptide moiety A and a C-terminal diaminoalcohol residue B that is initially or eventually bound to the moiety A by an amide bond, wherein (1) the diaminoalcohol B is:

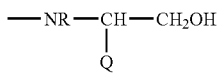

with Q being $(CH_2)_n$—$NH_2$, with n being 2, 3 or 4, and R being $CH_3$ or $C_2H_5$; and
(2) the moiety A is:

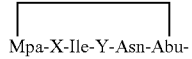

Some key intermediates that may be employed in the overall syntheses of interest include the α-alkylated diamino alcohol either as the free or protected alcohol or attached to a suitable resin by an ether bond, and the known compound "carba-6" described hereinafter. The invention also provides methods that are useful to produce these key intermediates which then can be effectively employed in efficient syntheses of these heptapeptide analogues.

The improved overall syntheses that have been developed for making these cyclic heptapeptide oxytocin antagonists result in simplification of steps, increased yields and/or lower costs of raw materials, thus rendering them much more desirable routes to the compounds of choice. These syntheses generally utilize such an alkylated diamino alcohol and the protected amino acid referred to as Fmoc-carba-6, i.e.,

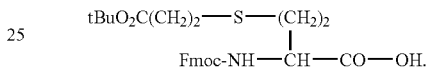

The intermediate Fmoc-carba-6 may be synthesized using a state-of-the-art method as disclosed in the '722 patent; however, an improved synthesis for this intermediate is hereinafter described.

The known synthesis for the intermediate Fmoc-carba-6, i.e. Fmoc-Abu(SCH$_2$CH$_2$CO$_2$t-Bu)OH that is disclosed in the '722 patent starts with the dimer of homocysteine, (Hcy)$_2$. However, the cost of this starting material is considerable, i.e. currently over about $250 for 5 grams. An improved synthesis for this intermediate, i.e., Fmoc-carba-6, has been developed which allows it to be economically synthesized through the use of readily available methionine (Met) as a starting material. The cost difference of starting materials is highly significant because the cost per mol of Met is about 50 times less. Methionine is first reduced by treatment with sodium in ammonia, and the resultant sulfhydryl group is then alkylated using either t-butyl acrylate or t-butyl 3-bromopropionate to add the moiety that eventually becomes the N-terminal residue of the heptapeptide. At this point, an $N^\alpha$-protecting group is routinely introduced. In addition to saving on raw material cost, it was found that, when performed on a large scale, the process results in a product that can be precipitated in crystalline form from a solution of ethyl acetate during evaporation, thus simplifying the purification process.

A novel intermediate used to build the C-terminal portion of the ultimate linear hexapeptide is an N-protected or unprotected, N-alkyl, β-amino alcohol derived from a protected α-amino acid where the α-carboxyl group has been transformed to an alcohol and may optionally be protected by a protecting group or be coupled to a resin. In other words, this intermediate is a diaminoalcohol which is defined to by the formula:

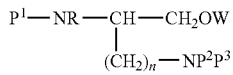

wherein $P^1$ is H or an amino-protecting group; $P^2$ is an amino-protecting group that is different than $P^1$ if $P^1$ is present and is not labile under conditions that would remove $P^1$; $P^3$ is H or an amino-protecting group that is different than $P^1$ and is not labile under conditions that would remove $P^1$, provided however that $P^2$ and $P^3$ may be a divalent amino-protecting group; n is 2, 3 or 4, R is alkyl; and W is H, a protecting group or resin. A suitable resin, such as a chlorotrityl resin, may be used, and the optional protecting agent may be one of those commonly used to protect Ser or Thr, e.g. TMS (trimethylsilyl). R is preferably methyl or ethyl and more preferably is methyl. The intermediates used in making the preferred cyclic equivalent heptapeptides are those wherein n is 3, i.e. the protected $N^\alpha$-methyl ornithinol; thus, this compound is a particularly preferred intermediate.

Briefly, it has been found that such a methyl ornithine alcohol can be efficiently synthesized by beginning with Orn, the side chain amino group of which is protected by benzyloxycarbonyl (Z) or by another suitable amino-protecting group that remains when the α-amino protecting group is removed; H-Orn(Z)-OH is a commercially available starting material. Other protected amino acids having either 2 or 4 methylene groups in the amino side chain can alternatively be employed to produce a different desired end product. Treatment with formic acid and acetic anhydride converts the α-amino group to a formamido moiety. Thereafter, treatment with boron hydride complexed in tetrahydrofuran reduces the α-carboxyl group to $CH_2OH$ and the formamide moiety to methylamino. If an ethylamino group is desired, the α-amino group of Orn is instead acetylated to add an acetyl group rather than a formyl group. Thereafter, if desired the α-amino group can be protected e.g. with Fmoc, and the compound can be coupled to a resin by an ether bond at the alcohol. Alternatively, Fmoc-Orn(Z)-ol may be linked to a 2Cl-Trt resin, as by reaction in DCM containing pyridine, and used to build a hexapeptide on the resin; Fmoc-Orn(Z)-ol is easily obtained from commercially available Fmoc-Orn(Z)-OH by reduction of its mixed anhydride with sodium borohydride.

In one overall synthesis for making the desired cyclic equivalent heptapeptides, Fmoc-carba-6 is linked to a 2-chlorotrityl chloride resin (2Cl-Trt resin) by reaction with the resin to form an ester bond with the α-carboxyl group while the side chain omega carboxy group and the α-amino group are protected. Other suitable resins might alternatively be used. The Fmoc protection is then removed from the α-amino group, and a pentapeptide is created by sequentially coupling with Fmoc-Asn, Fmoc-Y, Fmoc-Ile and then Boc-X. The side chains of Asn, X and/or Y may be protected if desired. For example, when X is D-Trp, it may be desirable to protect the indole nitrogen; however, the synthesis can be effectively performed without protecting either Asn or D-Trp. The use of Boc-protection for the last amino acid to be added allows for the later simultaneous cleavage of the t-butyl ester group protecting the side chain carboxy and the N-terminal protecting group.

At this point in the synthesis, the linear peptide is cleaved from the resin (as by treatment with a mixture of DCM/TFE/AcOH) to produce the pentapeptide having a free acid at its C-terminus. A reaction is then carried out to add H-MeOrn (Z)-ol at the C-terminus, preferably by a mixed anhydride method to reduce potential racemization of the Abu residue. If desired, the alcohol can be protected with a suitable protecting group, e.g. trityl, TMS or benzyl ether; for example, the reaction was successfully carried out after $N^\alpha$MeOrn(Z)-ol was converted to its N,O-bis(trimethylsilyl) derivative by the treatment with N,O-bis(trimethylsilyl)acetamide. However, it is felt that such a step is clearly optional and is not needed to protect against O-acylation. After this addition to create the hexapeptide is effected, deprotection is carried out using TFA in dichloromethane (DCM) with suitable scavengers, to simultaneously remove the Boc protection at the N-terminus and the t-butyl protection of the side chain carboxyl group. Cyclization is then effected to link the long side chain to the α-amino group of D-Trp and thereby create the equivalent heptapeptide, preferably being suitably carried out, e.g. in the presence of PyBOP and DIPEA in dimethyl formamide (DMF). Thereafter, the final deprotection of the side chain amino group of ornithinol is carried out using hydrogen fluoride or trimethylsilyl bromide with suitable scavengers to produce the cyclic, C-terminal alcohol, oxytocin antagonist equivalent heptapeptide, which can be purified by HPLC and converted to the acetate salt by ion exchange.

In an alternative overall synthesis, the desired cyclic equivalent heptapeptide alcohol is efficiently made by initially linking commercially available Fmoc-Orn(Z)-ol to a 2Cl-Trt resin as by reaction in pyridine. Thereafter, the Fmoc protection is suitably removed by treatment with an appropriate base, such as piperidine, and the α-amino group is alkylated on the resin, as by treatment first with o-NBS-Cl and 2,4,6-collidine in DCM, and then with the addition of a mixture of TPP, DIAD and MeOH. Various alkyl groups can be introduced by employing different alcohols. N-methylation can also be achieved by treating the o-NBS resin-bound alcohol with 3-5 eq. of methyl 4-nitrobenzene sulfonate and an appropriate base, such as MTBD. After alkylation is complete, final treatment with 2-mercaptoethanol and DBU in DMF removes the o-NBS. The resulting $N^\alpha$MeOrn(Z)-resin is then sequentially treated to stepwise construct the hexapeptide on the resin. The peptide can be built generally as indicated above, with the first coupling being with Fmoc-carba-6. By using DIC/HOBt coupling, protection of the side chain of Asn can usually be omitted. The Boc-hexapeptide-resin may then be cleaved and simultaneously selectively deprotected to remove the Boc and t-Bu protecting groups, as by treating with an aqueous solution of TFA and DCM containing TIS. Final cyclization to create the cyclic equivalent heptapeptide and deprotection may then carried out as known in the art. The product is isolated and purified using standard techniques, and only a single purification step, followed by ion-exchange, is required. It can be seen that, by taking advantage of the two intermediates, the overall synthesis is greatly simplified and can be economically performed in high yield.

More specifically, the just-described synthesis would generally include the following steps:

(a) providing a resin-linked diamino alcohol having the formula:

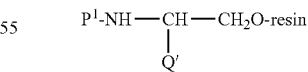

wherein $P^1$ is H or an amino-protecting group, such as Fmoc or o-NBS, Q' is $(CH_2)_n$—$NP^2P^3$, with n being 2, 3 or 4, $P^2$ being an amino-protecting group that is different from $P^1$ and not labile under conditions that would remove such a $P^1$ protecting group, and $P^3$ being H or an amino-protecting group that is the same or different than $P^2$, provided however that $P^2$ and $P^3$ may be a divalent amino-protecting group, and wherein the resin is one capable of forming an ether bond with an aliphatic alcohol;

(b) replacing P¹ with o-NBS if P¹ is present as other than o-NBS or adding o-NBS, and then N-alkylating to produce the compound

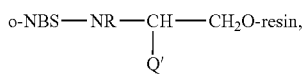

wherein R is CH₃ or C₂H₅;

(c) removing o-NBS and adding residues either singularly or in a group or groups to create the following peptide-resin:

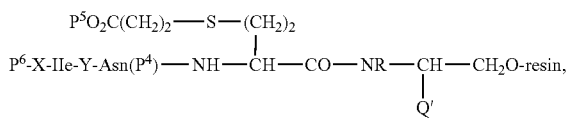

wherein

P⁴, P⁵ and P⁶ are individually H or protecting groups and X and Y are as defined above;

Note: This compound may also be written as:

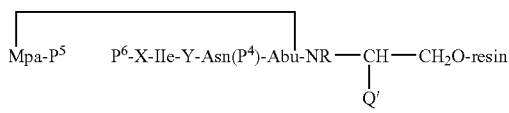

(d) cleaving from the resin and simultaneously selectively deprotecting to form the linear compound:

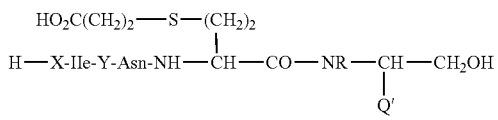

(e) cyclizing the linear compound to create the compound:

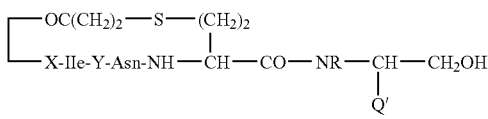

(f) deprotecting to create the cyclic equivalent heptapeptide:

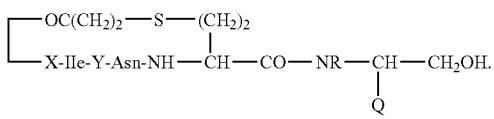

The following specific examples describe detailed syntheses of compounds of interest according to the foregoing general outline. They contain the best modes of these syntheses and are considered to be representative of the synthesis of compounds of interest in accordance with the present invention; however, they should not be construed to constitute limitations upon the invention which is defined in the claims appended hereto.

The following abbreviations are used:
TBTU 2-(1-H-benzotriazol-1-yl)-1,1,3,3-tetramethyl-uronium tetrafluoroborate
PyBOP benzotriazole-1-yl-oxy-tris-pyrrolidino phosphonium hexafluorophosphate DIPEAN,N-diisopropyl ethyl amine
DIC 1,3-diisopropyl carbodiimide
Boc tert-butyloxycarbonyl
Z benzyloxycarbonyl
Fmoc 9-fluorenylmethyloxycarbonyl
o-NBS-Cl o-nitrobenzenesulfonyl chloride
TFA trifluoroacetic acid
DCM dichloromethane
EDT ethanedithiol
DMF dimethylformamide
THF tetrahydrofuran
MTBD 7-methyl-1,5,7-triazabicyclo[4,4,0]dec-5-ene
BH₃ THF borane-tetrahydrofuran complex
DME 1,2 dimethoxyethane
TIS triisopropylsilane
DBU 1,8-diazabicyclo[5.4.0]undec-7-ene
MeCN acetonitrile
TPP triphenylphosphine
TFE trifluoroethanol
TEAP triethylammonium phosphate
EtOAc ethyl acetate
DIAD diisopropyl azodicarboxylate
TMSBr trimethylsilyl bromide
AcOH acetic acid
MeOH methanol
NMM N-methymorpholine
Ac₂O acetic anhydride
Et₂O ethyl ether
Ac₂O acetic anhydride
FmocONSu N-(9-fluorenylmethoxycarbonyloxy)succinimide

EXAMPLE I

Synthesis of N$^\alpha$MeOrn(Z)-ol 444.7 g (1.67 mole) of commercially available H-Orn(Z)-OH was dissolved in 3.5 L (93 moles) of formic acid. The solution was cooled in an ice bath, and 1.17 L (12 moles) of acetic anhydride was subsequently added in dropwise fashion over two hours while the temperature of the reaction mixture was maintained between about 5° and 15° C. The resultant reaction mixture was stirred at room temperature for about two hours after the addition was completed, and the reaction vessel was refrigerated overnight. 1.5 L of cold water was then added, and the solution was concentrated to dryness under reduced pressure. The residual, light yellow syrup was taken up into EtOAc, washed with water and then with saturated NaCl, and then dried overnight over sodium sulfate. After filtration and evaporation to dryness, the residual syrup was dissolved in 5 L of ethyl ether. The solution was cooled in a dry ice bath and seeded. The resulting crystalline product was filtered, washed with ethyl ether, air dried for two hours and finally dried in a lyophilizer. 431.6 g (1.47 mole, 88%) of For-Orn(Z)-OH was obtained.

353.2 g (1.2 mole) of dry For-Orn(Z)-OH was placed in a 10 L three-necked round-bottom flask equipped with a condenser and an external ice bath. 4 L (4 mole) of a reducing agent, 1 molar BH₃THF in THF, was added over 30 minutes. An exothermic reaction took place immediately with the release of hydrogen gas. A clear, refluxing solution resulted, and the reaction mixture was stirred overnight. Because the reaction was incomplete (HPLC) analysis), an additional 1 L (1 mole) of 1 molar $BH_3THF$ in THF was added, and the mixture was stirred at room temperature for about 2 hours, at the end of which period, the completion of the reaction was evident. The reaction was then quenched with 1 L of methanol, and the solvents were evaporated. The residue was redissolved in 600 mL of methanol and evaporated. The residual oil was partitioned between 1.5 L of water and 0.8 L of DCM, and the pH was adjusted to about 2 with HCl. The water phase was separated and washed with DCM (3×0.8 L), and subsequently the pH was adjusted to 12 with 5 molar NaOH. The product was extracted with DCM (3×1.5 L). The combined extracts were washed with aqueous NaCl and dried over sodium sulfate. The drying agent was filtered off, and the solvent was evaporated. The residue was taken up in 0.5 L of ethyl ether, and seed crystals were added. 149 g (0.56 mole, 47%) of a white crystalline product was obtained, which product upon analysis was confirmed to be the desired $N^\alpha$Me-Orn(Z)-ol.

The foregoing shows that reduction using $BH_3THF$ complex was effective to reduce both the formyl group to methyl and the α-carboxyl group to $CH_2OH$.

EXAMPLE II

Synthesis of Carba-6

The modified and protected homocysteine residue that initially forms residue 5 of the hexapeptide is sometimes referred to "carba-6". As indicated hereinbefore, it has the chemical formula Fmoc-Abu($SCH_2CH_2CO_2$t-Bu)OH. An efficient synthesis has been designed beginning with commercially available methionine.

Ammonia (5 L) was condensed into a flask containing 2 moles of Met. About 6.15 moles of sodium were added piece by piece to create the sulfhydryl group at the end of the side chain. Addition was continued until blue color persisted for 20 minutes. Ammonium chloride (2.1 mol) was added to the reaction mixture to neutralize sodium amide formed. The resulting clear solution was left overnight under a stream of nitrogen to remove ammonia. The solid residue (L-homocysteine and inorganic salts) was dissolved in 15 L of degassed water, and the solution was adjusted to pH 8.1 with hydrochloric acid under nitrogen. To the resulting solution t-butyl acrylate (4 mol) was added dropwise, and the reaction mixture was stirred overnight under nitrogen. The solid product formed was collected by filtration, washed with water and t-butyl-methyl ether to give crude S-(2-tertbutoxycarbonylethyl)-homocysteine, i.e. its sulfhydryl group being substituted with a protected propionyl group. The crude product (1.53 mol) was suspended in water, and saturated sodium bicarbonate solution was then added followed by THF. Then 5 M NaOH was delivered from an autotitrator, at pH not exceeding 10, until a clear solution was obtained. To this solution, a suspension of FmocONSu (1.68 mol) in THF was added portionwise while pH, after an initial drop, was kept at 7.5-8 by delivering 5 M NaOH from autotitrator. The reaction mixture was stirred for 4 hours and left in a refrigerator overnight. THF was evaporated, and the residue was extracted with ether. Three layers were formed. The middle one, which was found to contain the desired product, was collected. It was determined by HPLC that the middle layer contained 5-10% of the major by-product (Fmoc-Hcy)$_2$. To convert it to the desired product, the middle layer was diluted with water, tributylphosphine was added to the resulting solution, and the reaction mixture was stirred for 45 minutes followed by extraction with ether. To the aqueous layer t-butyl acrylate was added, and the mixture was stirred overnight. After washing with ether, the aqueous solution was acidified to pH 2 with 6 M HCl, and the product was extracted with ethyl acetate. The extract was dried and concentrated in vacuo. Upon evaporation of ethyl acetate, the product, Fmoc-carba-6, started to crystallize. At this point, the concentrated ethyl acetate solution was diluted with ether and then with hexane. The precipitate was collected, washed with a 1:1 mixture of ether and hexane and dried in vacuo to give the final product as a white solid. More product was recovered from the mother liquors to provide a total (from Met) of 625.6 g (1.29 moles) for a 64% yield.

The procedure is straightforward, gives good yields and good purity after a single crystallization. There is no need for preparing a DCHA salt intermediate as described in the literature.

EXAMPLE III

Synthesis of Cyclic Heptapeptide

One improved synthesis of these heptapeptides of interest initially builds a pentapeptide on a 2Cl-Trt resin and is described hereinafter.

Fmoc-protected carba-6 was coupled to a resin by nucleophilic displacement of the chlorine ion in the presence of DIPEA. Cleavage of the Fmoc group was then carried out using 25% piperidine in DMF for 30 minutes. Thereafter, the next four amino acids, e.g. Asn, aIle, Ile and D-Nal were sequentially added, each time using about a 2.5 molar excess of Fmoc-AA (or Boc-AA for the N-terminus) and converting the amino acid to its HOBt ester and using an equimolar amount of DIC; coupling took place at room temperature over about 2 hours. Upon completion of the pentapeptide, cleavage from the resin took place by treatment with a mixture of acetic acid, TFE and DCM, at a ratio of 1 part/2 parts/7 parts, for about 1½ hours at room temperature, leaving the protecting groups in place, which facilitate the next coupling at the C-terminus.

Next the pentapeptide was coupled with $N^\alpha$MeOrn(Z)-ol (see Example I) using the mixed anhydride method in order to reduce potential racemization of the Abu residue. The mixed anhydride was generated from the peptide and isobutyl chloroformate in the presence of NMM, and coupling readily proceeded. The crude hexapeptide was isolated by aqueous workup and lyophilized from t-butanol.

The crude hexapeptide was then treated with TFA/DCM (1:1) containing about 2% of TIS, for about 1 hour, to remove the Boc-protecting group at the N-terminus and the t-butyl based protecting group on the Abu residue side chain. After evaporation of the solvents, it was lyophilized from an aqueous mixture containing about 60% MeCN and about 0.1% TFA. Cyclization was then carried out in DMF at the concentration of about 1.5 millimole per liter of the crude peptide, using PyBOP in the presence of DIPEA. After completion of the reaction, the solvents were evaporated, and the residue was lyophilized from t-butanol. Removal of the Z-protecting group was then accomplished using HF at 0° C. for about 1 hour. The crude peptide was then precipitated with ethyl ether, and lyophilized from an aqueous solution of acetonitrile.

Final purification of the cyclic equivalent heptapeptide was carried out on a C18 HPLC cartridge using a TEAP system at a pH of about 2.3. The fractions containing the pure peptide were pooled and reapplied to a C18 cartridge, which was then washed with about 5 volumes of 0.1 molar ammonium acetate in order to obtain the acetate salt. Final elution was carried out with 2% acetic acid/acetonitrile system, and the fractions containing the pure product were pooled and lyophilized. Mass spectrometry (electro spray ionization, ion trap analysis, positive mode) indicated a molecular mass in agreement with the calculated mass of the expected structure, i.e. measured m/z equals 841.5; calculated m/z equals 841.5.

The overall method produces high yield, and the final purification is straightforward. As an alternative to deprotecting with HF, one might use a cocktail of TMSBr/thioanisole/TFA/EDT(1:1:6:0.5).

Oxytocin Receptor Binding Assay

Recombinant human oxytocin receptors were expressed in CHO cells using standard molecular biological techniques. A membrane fraction was prepared and incubated in the presence of [$^{125}$I]-oxytocin and varying concentrations of equivalent heptapeptide analogue. Membranes were then isolated by filtration and counted for radioactivity to determine oxytocin binding. An inhibition constant $K_i$ was determined for the analogue. The results obtained showed a value of 0.1 nM, which is considered to be excellent. Similar results were obtained using such receptors expressed in HEK293 cells.

EXAMPLE IV

Alternative Synthesis of Cyclic Equivalent Heptapeptide

Another synthesis for these equivalent heptapeptide alcohols was derived in order to further simplify the overall procedure and to avoid the need to prepare MeOrn(Z)-ol or Fmoc-MeOrn(Z)-ol. The synthesis initially directly attaches Fmoc-Orn(Z)-ol to 2-Cl-Trt resin. The hexapeptide is subsequently assembled, and it is cleaved as a linear peptide and simultaneously selectively deprotected and thus is ready to be cyclized. This approach reduces the risk of racemization as a G+1 coupling is not necessary.

1) Synthesis of Fmoc-Orn(Z)-ol

Commercially available Fmoc-Orn(Z) was converted to the alcohol by reduction of its mixed anhydride with sodium borohydride. After crystallization from EtOAc, the compound was thereafter used without further purification.

2) Attachment of Fmoc-Orn(Z)-ol to resin.

1.06 g of 2-Cl-Trt resin (1.39 mmol) was preswollen in DCM, and a solution of Fmoc-Orn(Z)-ol (0.84 mmol) and 5 eq of pyridine in 10 ml of DCM was added. The disappearance of the alcohol was monitored by HPLC to determine the progress of the reaction.

A sample of the reaction mixture was saved to assess the stability of the Fmoc group under the reaction conditions. The Fmoc group was found to be sufficiently stable under the conditions used. The reaction was allowed to proceed for approximately 36 hours to achieve substitution of approximately 0.5 mmol/g of 2-Cl-Trt resin.

3) Alkylation on the resin.

The Fmoc group was then removed with 25% piperidine in DMF. The compound was first treated with o-NBS-Cl in the presence of 2,4,6-collidine in DCM to convert the α-amino group into a sulfonamido group that is suitably reactive. After 1 hour, the ninhydrin test was negative, and the resin was then washed with DMF and DME. The resin-bound sulfonamide was then treated with MeOH/DIAD/TPP, 10 equivalents, overnight, using DME as a solvent, causing the amino group to be alkylated. Aliquots of the resin before and after alkylation were cleaved with 50% TFA/DCM, and the samples were analyzed by HPLC. Alkylation was deemed to be complete, and the o-NBS group was removed by treatment with 2-mercaptoethanol and DBU in DMF.

4) Building the linear peptide.

Five residues were then sequentially added as in Example III, substituting Boc-D-Trp for Boc-D-Nal. No HOBt was used in the coupling of Fmoc-carba-6.

5) Cyclization of the Equivalent Heptapeptide.

The hexapeptide was cleaved from the resin and simultaneously selectively deprotected by treatment with TFA/DCM (1:1) and 1% of TIS to produce the compound H-D-Trp-Ile-aIle-Asn-Hcy((CH$_2$)$_2$COOH)-MeOrn(Z)-ol. Cyclization was then carried out as in Example III by treatment with PyBOP and DIPEA in DMF. Once cyclization was complete, the final protecting group was removed by treatment with a TFA/TMSBr/thioanisole cocktail. Purification was then carried out as in Example III using HPLC, and the peptide was converted to its acetate salt. Mass spectrometry indicated a molecular mass in agreement with the calculated structure, i.e. measured m/z equals 830.5; calculated m/z equals 830.5.

This procedure employs a minimum number of steps and a single purification and is considered to be highly efficient and economical. An inhibition constant $K_1$ for binding in the oxytocin receptor assay was determined and found to be 0.1 nM, essentially the same as for the peptide resulting from Example III, confirming the apparent interchangeability of the D-Trp and D-Nal residues in these analogues.

Although the foregoing description and the examples provide the best mode presently known to the inventors for carrying out their invention, it should be understood that various changes and modifications as would be apparent to one skilled in this art may be made without departing from the scope of the invention which is set forth in the claims appended hereto. For example, although the description has been focused on certain preferred compounds, particularly ones which incorporate a derivative of ornithine at the C-terminus, it should be understood that similar α-amino acids having longer or shorter side chains might be employed if desired without departing from the process. The disclosures of the previously enumerated patents are expressly incorporated herein by reference.

Particular features of the invention are emphasized in the claims that follow.

The invention claimed is:

1. A method for preparing a peptide or a pharmaceutically acceptable salt thereof, having oxytocin antagonist activity and consisting of a moiety A and a residue B having a C-terminal β-aminoalcohol which is bound to the moiety A by an amide bond,
wherein (1) said residue B is:

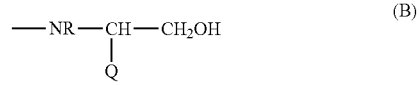

(B)

with Q being (CH$_2$)$_n$—NH$_2$, with n being 2, 3 or 4 and R being CH$_3$ or C$_2$H$_5$; and (2) said moiety A is:

(A)

with Mpa, Ile, Asn and Abu having the following meanings:

Mpa 3-mercaptopropionic acid residue
Ile isoleucine residue
Asn asparagine residue
Abu α-aminobutyric acid residue;
with X being a D-aromatic α-amino acid, which may optionally have its side chain protected, and
with Y being an aliphatic α-amino acid; which method includes the following steps:

(a) reacting an α-amino acid having a protected amino side chain and an acylated α-amino group with a reducing agent to change the acyl group to an alkyl group and to simultaneously change the α-carboxy group to $CH_2OH$ to provide a diamino alcohol having the formula:

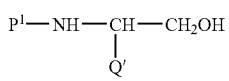

wherein $P^1$ is H or an amino-protecting group; and $Q'$ is $(CH_2)_n$—$NP^2P^3$, with n being 2, 3 or 4, $P^2$ being an amino-protecting group that is different from $P^1$ and not labile under conditions that would remove $P^1$, and $P^3$ being H or an amino-protecting group that is the same or different than $P^2$, provided however that $P^2$ and $P^3$ may be a divalent amino-protecting group;

(b) reacting said product of step (a) with the pentapeptide:

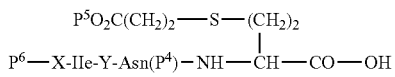

wherein $P^4$, $P^5$ and $P^6$ are individually protecting groups to form the linear hexapeptide:

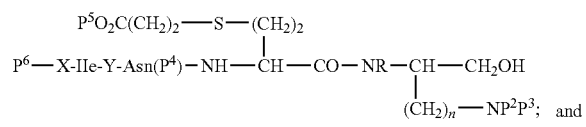

c) selectively deprotecting and cyclizing the linear compound of step(b) to create the heptapeptide:

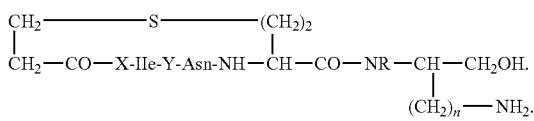

2. The method of claim 1 wherein, in step (a), said reaction of said α-amino acid having the protected amino side chain and the acylated α-amino group to change the acyl group to an alkyl group and to simultaneously change the α-carboxy group to $CH_2OH$ is a reaction with a reducing agent.

3. The method of claim 1 wherein, said reaction in step (a) is between ornithine, having its side chain amino group protected and its α-amino group formylated, and a reducing agent in a suitable solvent to simultaneously change the formyl group to a methyl group and to change the α-carboxyl group to $CH_2OH$.

4. The method of claim 1 wherein, prior to step (a), a reaction is with ornithine, having its side amino chain group protected, formic acid and acetic anhydride to formulate said α-amino acid having a protected amino side chain and an acylated α-amino group, and thereafter in step (a) the reaction is with a reducing agent in a suitable solvent to simultaneously change the formyl group to a methyl group and to change the α-carboxyl group to $CH_2OH$.

5. The method of claim 4 wherein said reducing agent is $BH_3THF$.

6. A method for preparing a peptide, or a pharmaceutically acceptable salt thereof, having oxytocin antagonist activity and consisting of a hexapeptide moiety A and a residue B having a C-terminal β-aminoalcohol which is bound to the moiety A by an amide bond, wherein (1) said residue B is:

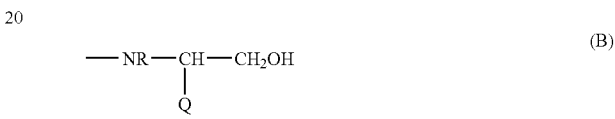

with Q being $(CH_2)_n$—$NH_2$, with n being 2, 3 or 4 and R being $CH_3$ or $C_2H_5$; and (2) said moiety A is:

with Mpa, Ile, Asn and Abu having the following meanings:

Mpa 3-mercaptopropionic acid residue
Ile isoleucine residue
Asn asparagine residue
Abu α-aminobutyric acid residue;
with X being a D-aromatic α-amino acid, which may optionally have its side chain protected, and
with Y being an aliphatic α-amino acid;

which method includes the following steps:

(a) providing a resin-linked amino acid having the formula:

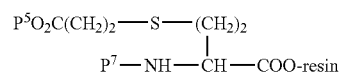

wherein $P^5$ is a protecting group and $P^7$ is H or a protecting group;

(b) adding residues either singularly or in a group or groups to create the following pentapeptide-resin:

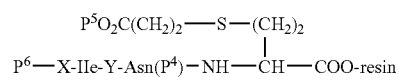

wherein $P^4$ is H or a protecting group and $P^6$ is a protecting group;

(c) cleaving the pentapeptide-resin to form the linear free acid pentapeptide:

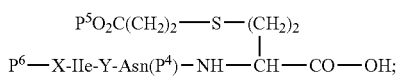

(d) coupling

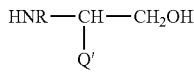

to the product of step (c) to form the linear hexapeptide:

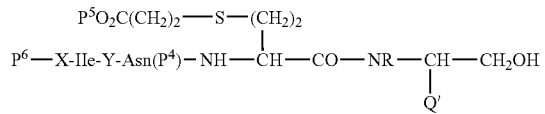

wherein Q' is $(CH_2)_n$—$NP^2P^3$, with n being 2, 3 or 4, $P^2$ being an amino-protectingg group, and $P^3$ being H or an amino-protecting group that is the same or different than $P^2$, provided however that $P^2$ and $P^3$ may be a divalent amino-protecting group;

(e) selectively deprotecting and cyclizing the linear compound resulting from step (d) to create the partially protected cyclic peptide:

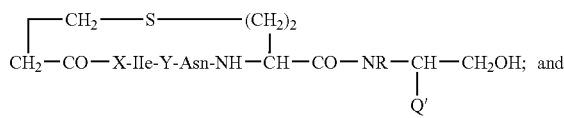

(f) further deprotecting the moiety Q' to create the cyclic peptide:

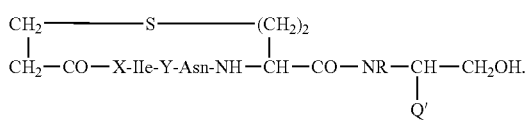

7. The method of claim 6 wherein X is D-Trp or D-Nal, Y is aIle and n is 3.

8. The method of claim 1 wherein $P^3$ is H.

9. The method of claim 4 wherein $P^3$ is H.

* * * * *

UNITED STATES PATENT AND TRADEMARK OFFICE
CERTIFICATE OF CORRECTION

| | | |
|---|---|---|
| PATENT NO. | : 7,816,489 B2 | Page 1 of 1 |
| APPLICATION NO. | : 11/929494 | |
| DATED | : October 19, 2010 | |
| INVENTOR(S) | : Kazimierz Wisniewski et al. | |

It is certified that error appears in the above-identified patent and that said Letters Patent is hereby corrected as shown below:

At column 18, line 53, "COO-resin" should read -- CO-resin --.

At column 18, line 63, "COO-resin" should read -- CO-resin --.

At column 19, line 23, "protectingg" should read -- protecting --.

Signed and Sealed this
Twenty-fifth Day of January, 2011

David J. Kappos
*Director of the United States Patent and Trademark Office*